Figure 1:
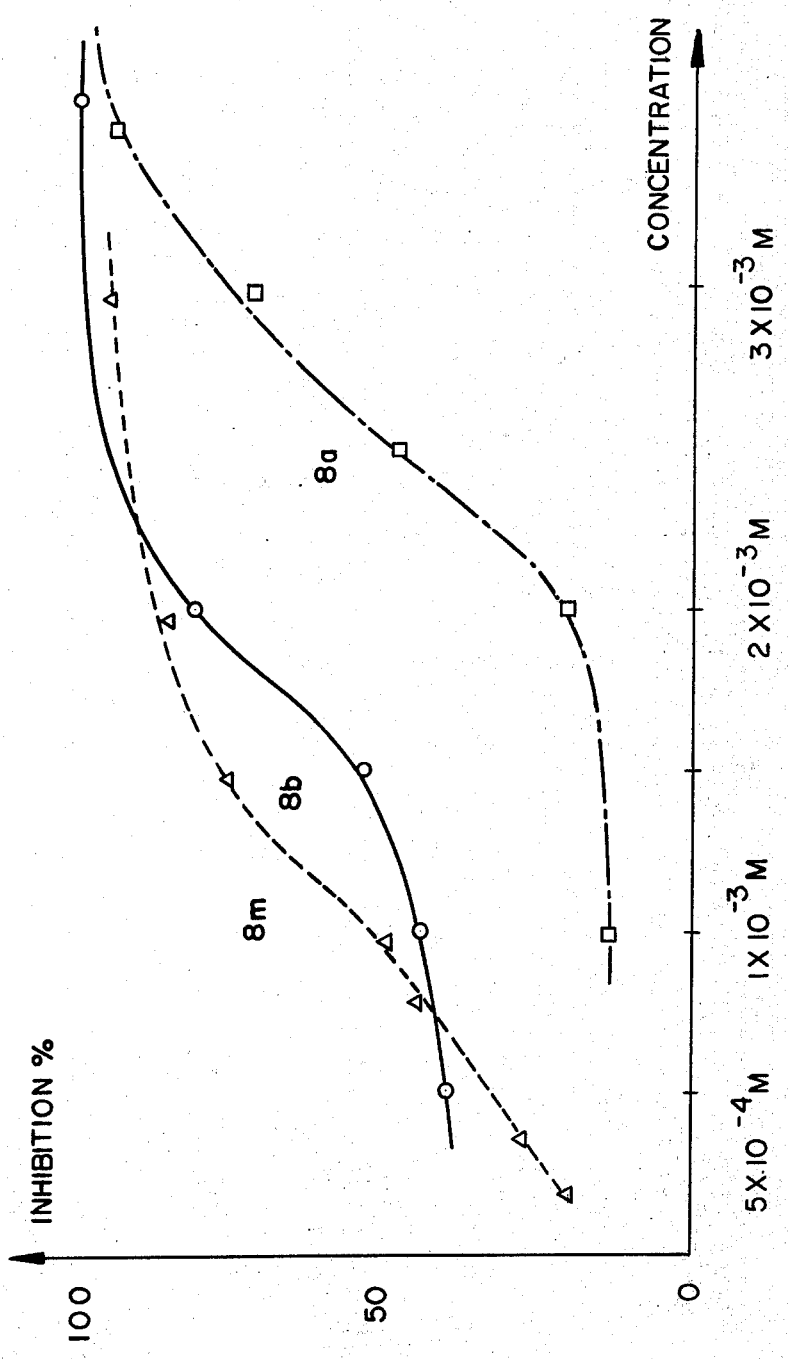

United States Patent
Devaux et al.

[11] 3,993,470
[45] Nov. 23, 1976

[54] PROCESS FOR CONTROLLING THE GROWTH OF DICOTYLEDONS

[75] Inventors: Bernard Devaux, Villeurbanne; Henri Pacheco, Lyon, both of France

[73] Assignee: Agence Nationale de Valorisation de la Recherche (ANVAR), Neuilly-sur-Seine, France

[22] Filed: Mar. 14, 1975

[21] Appl. No.: 558,437

[30] Foreign Application Priority Data
Mar. 13, 1974 France .............................. 74.08457

[52] U.S. Cl. ..................................... 71/94; 71/76; 71/95; 71/117; 71/120; 260/293.65; 260/293.76; 260/293.78; 260/293.86; 260/293.87
[51] Int. Cl.² .......................................... A01N 9/22
[58] Field of Search ...... 71/94; 260/293.65, 293.78, 260/293.87; 424/267

[56] References Cited
UNITED STATES PATENTS

| | | | |
|---|---|---|---|
| 2,167,351 | 7/1939 | Eisleb | 260/293.78 |
| 3,065,134 | 11/1962 | Maillard et al. | 424/267 |
| 3,506,434 | 4/1970 | Jacobi et al. | 71/94 |

FOREIGN PATENTS OR APPLICATIONS

| | | | |
|---|---|---|---|
| 7,123,738 | 7/1971 | Japan | 260/293.78 |

*Primary Examiner*—Glennon H. Hollrah
*Attorney, Agent, or Firm*—Eric P. Schellin

[57] ABSTRACT

This invention relates to a herbicidal composition comprising an effective amount of a compound of the formula:

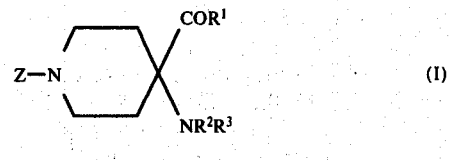

in which Z is a hydrogen atom or a benzyl group optionally substituted at para-position with a halogen atom, $R^1$ is either a group -OR in which R is an alkyl group having 1-12 carbon atoms, a cyclohexyl or a lower phenylalkyl group, or a hydrazino group, $R^2$ and $R^3$ represent a hydrogen atom, a benzyl group, a group $-COR^4$ in which $R^4$ is a phenyl, lower alkyl or anilino group or $R^2$ and $R^3$, together with the nitrogen atom to which they are attached, form a phthalimido or succinimido group, and their acid addition salts. This composition has in particular an inhibiting activity on the growth of some dicotyledons.

3 Claims, 2 Drawing Figures

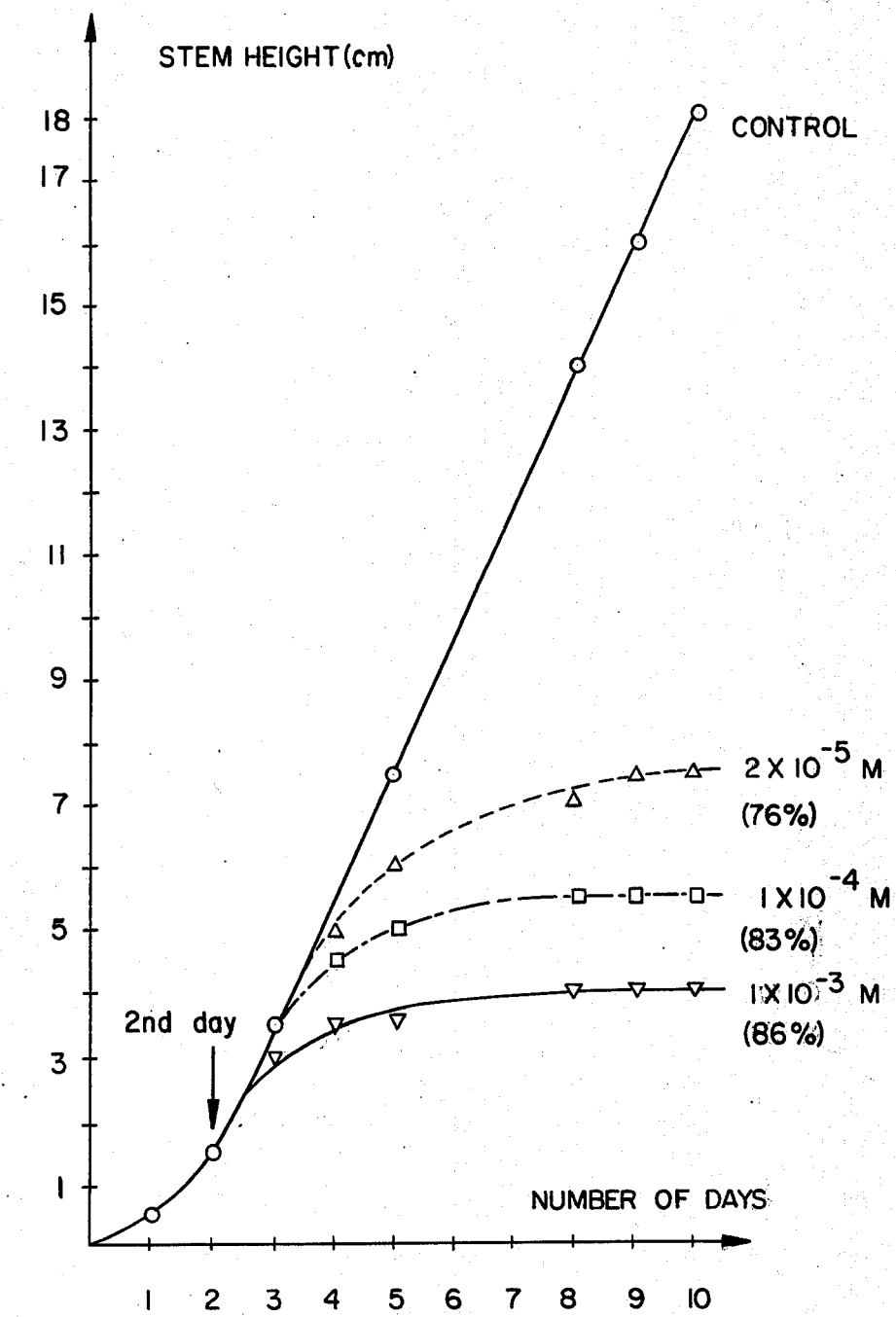

PROCESS FOR CONTROLLING THE GROWTH OF DICOTYLEDONS

This invention relates to new herbicides, viz., isonipecotic acid derivatives, having an inhibiting activity on the growth of some dicotyledons, and to a process for their preparation.

Said herbicides are compounds having the formula:

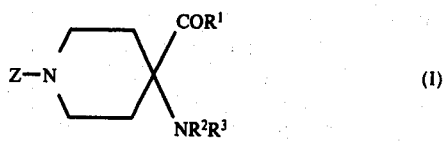

in which:
- Z is a hydrogen atom or a benzyl group optionally substituted at para-position with a halogen atom,
- $R^1$ is either a group —OR in which R is an alkyl group having 1–12 carbon atoms, a cyclohexyl or lower phenylalkyl group, or a hydrazino group,
- $R^2$ and $R^3$ represent each a hydrogen atom, a benzyl group, a group —$COR^4$ in which $R^4$ is a phenyl, lower alkyl or anilino radical or, together with the nitrogen atom to which they are attached, form a phthalimido or succinimido group, and their acid addition salts.

Said compounds are new, except the lower alkyl 4-amino-isonipecotates mentioned in Chemical Abstracts 75, 110 315 n by Nakanishi as intermediates in the synthesis of spirohydantoin derivatives.

The compounds of the formula (I) are prepared by a novel process, from piperidyl-spirohydantoin derivatives of the formula

in which A is a hydrogen atom or a halogen atom, particularly a chlorine atom.

This process comprises first submitting the spirohydantoin to a hydrolysis with excess baryta, to give a compound of the formula

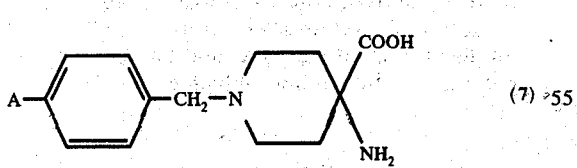

in which A has the aforementioned meaning. This hydrolysis may be effected typically by refluxing during about 100 hours or at 160° C under saturating vapour pressure during 3 hours.

The resulting aminoacid is then esterified by heating with an alcohol of the formula ROH in which R has the aforesaid meaning, this alcool being anhydrous with gaseous hydrogen chloride, to give a compound of the formula:

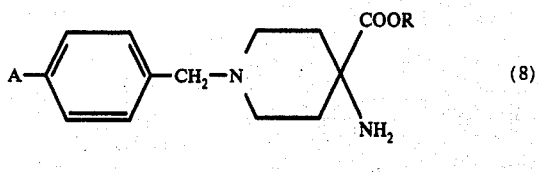

Said esters are converted to the other compounds of the formula (I) according to conventional methods. Thus, the diaminoesters may be N-acetylated by heating with their weight of sodium acetate in a large excess of acetic anhydride.

The N-benzoylation of the diamino-esters is readily effected in toluene, by action of benzoyl chloride, in the presence of triethylanine.

The diamino-esters treated with phthalic anhydride in toluene solution give, after a heating period of about 15 hours, alkyl 4-(N-phthalimido)-1-benzyl isonipecotates. The same technique may also be employed with succinic anhydride to prepare alkyl 1-benzyl-4-(N-succinimido)-isonipecotates.

On the other hand, phenyl isocyanate reacts with said diaminoesters to give corresponding alkyl 1-benzyl-4-(phenylureido)isonipecotates.

Finally, these different alkyl 4-amino-1-benzyl-isonipecotates may be N-debenzylated by catalytic hydrogenolysis over palladium.

The spirohydantoin of the formula (6) in which A is hydrogen is a known compound (G. Winters, V. Aresi and Nathanson, Farmaco Ed. Sci., 25 (9) 681–93 (1970).

The piperidyl spirohydantoins of the formula (6) may be obtained in good yield by a four-step procedure, from benzylamine (1) and methyl acrylate (2) according to the following reaction scheme:

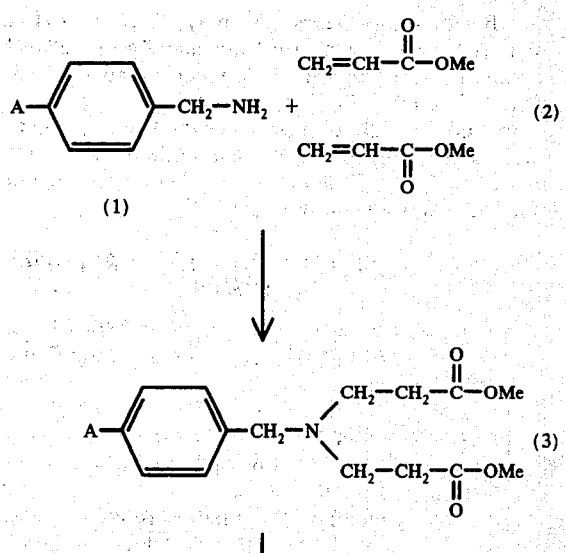

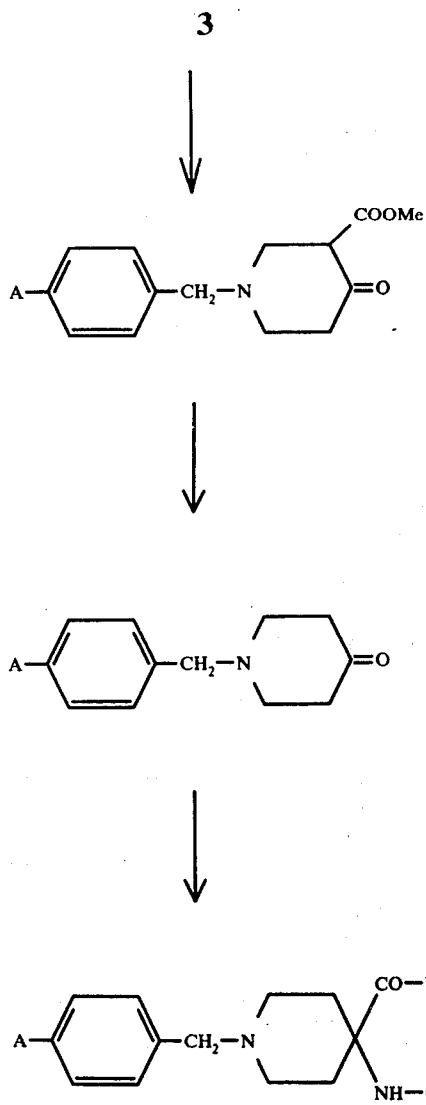

1-Benzyl-4-piperidone (5) may be converted to 8-benzyl-1,3,8-triazaspiro(4,5)decane-2,4-dione (6) by a Bucherer reaction (H. T. Bucherer and V. Lieb, J. Prakt. Chemie, 141, 5–43 (1934).

Indeed, like all ketones, 1-benzyl-4-piperdone reacts with sodium cyanide and ammonium carbonate, in aqueous-alcoholic medium, to give the corresponding piperidyl-spirohydantoin (6).

BIOLOGICAL TESTS ON THE HERBICIDAL ACTIVITY

The classes of tests were used to investigate the action of alkyl 4-amino-1-benzyl isonipecotates on the growth of plants:

Pre-emergence tests, comprising treating the seeds with the test material, prior to their germination, and which, therefore, make it possible to find inhibitors for the germination of the seeds;

post-emergence tests, which disclose the compounds which slow down or inhibit completely the growth of stems or roots. In such tests, the seeds are treated with the test material only after their germination.

The various herbicidal tests were conducted with a member of the Monocotyledons class, rye-Grass, and with a dicotyledon of the Lignoseae group, *Lens esculenta* (lentil).

PRE-EMERGENCE TESTS 3 g samples of Ray-Grass or 5 g samples of lentils are weighed out and immersed, during 24 hours, in 50 ml tap water (controls) or in 50 ml of a solution, of known concentration, of the test material. The seeds are then carefully spread over a layer of cotton-wool, in a Petri dish, and are watered with the liquid they have not absorbed.

The seeds are maintained 48 hours in the darkness, and are then exposed to light. They are watered daily with 20 ml tap water. The growth of the stems may be observed by daily measurements. After ten days exposure to light, the stems are cut level with the seeds and are then weighed.

The lentils treated only with water (controls) give 15–18 cm high stems, whereas the seeds treated with a herbicidal composition give more or less high stems, depending on the activity and the concentration of the particular herbicide.

The herbicidal activity of the test material is defined, with respect to the growth of the control seeds, by the expression:

$$\% \text{ inhibition} = \frac{(\text{weight of control stems}) - (\text{weight of treated stems})}{(\text{weight of control stems})} \times 100$$

It has appeared preferable to express the percent inhibition in terms of the weight of the stems rather than in terms of their height, because of the great variety of stem heights within a given test.

POST-EMERGENCE TESTS

The lentils (5 g) are immersed during 24 hours in 50 ml tap water and then spread out over a layer of cotton-wool and are left two days in the dark, prior to exposure to light.

At various times after the beginning of germination, the seeds and the stems obtained therefrom are sprayed with 10 ml of a solution, of known concentration, of the test material.

The products which are inactive on the multiplication of the stem cells have no influence on the growth of the plantlets, whereas the herbicidal compounds cause a marked slow-down, which may attain complete interruption, of the growth of the stems. The stems are cut and weighted after a high exposition of 10 days.

RESULTS

Pre-emergence tests

Ethyl 4-amino-1-benzyl-isonipecotate (8b) dioxalate possesses a growth inhibiting activity in lentils which is superior to that of Diuron, a commonly used herbicide, at concentrations of $10^{-3}$ to $4 \times 10^{-3}$M, while its action on rye-grass is much lower at the same concentrations.

It was first ascertained that this "herbicidal" activity was actually due to the ethyl 4-amino-1-benzyl-isonipecotate residue and not to the two oxalic acid molecules associated therewith. This verification was effected by modifying the nature of the anion associated with the diaminoester (8b) and by testing the growth inhibiting activity in lentils of the various salts thus prepared.

It was then attempted to discover the influence of the radical which esterifies the carboxylic function of 4-amino-1-benzyl isonipecotic acid (7).

To be able to effect a comparison between the herbicidal activity of these various diamino-esters, one was led to define a 37 50% inhibiting dose "(I.D.50), corresponding to the concentration of product which causes a 50% inhibition of the growth of the stems. The determination of these 50% inhibiting doses requires the plotting of curves giving the percent growth inhibition of the stems as a function of the herbicide concentration, and that for each product synthesized. The curves thus plotted have a sigmoid aspect.

The determination of the I.D.50 from the curves illustrated in FIG. 1 is sufficiently accurate and the reproductivity of the results is acceptable.

The percent inhibition on the growth of lentils (Dicotyledons) of methyl (8a), ethyl (8b) and dodecyl (8m) 4-amino-1-benzyl isonipecotates, respectively, are plotted in FIG. 1.

The values of the inhibiting doses 50% of the different alkyl 4-amino-1-benzyl isonipecotates and of the derivatives of said esters are tabulated in Tables 1 and 2 together with those of 2-4-D (sodium 2,4-dichlorophenoxyacetate) and Diuron [3-(3,4-dichloro-phenyl)-1,1-dimethyl urea].

It is apparent from Table 1 that the herbicidal activity of alkyl 4-amino-1-benzyl isonipecotates (8) is closely related to the nature of the alkyl group which esterifies the carboxyl function, since the cyclohexyl ester (8n) is 6500 times more active on the growth of lentils than the methyl ester (8a). It should also be noted that the inhibiting activity is much lower in the case of monocotyledons (Rye-Grass) than in the case of dicotyledons (lentils): the I.D.50 values obtained with Rye-Grass are indeed all above $10^{-4}M$ and even frequently above $10^{-3}M$, whereas those obtained with Lentils vary from $4 \times 10^{-7}M$ to $2.5 \times 10^{-3}M$.

It is also apparent from Table 1 that the herbicidal activity on the growth of lentils increases with the length of the straight alkyl chain up to the 1-pentyl ester (8g) which is one thousand times more active than the corresponding methyl ester (8a) and then decreases on further extension of the aliphatic chain.

The most active material, however, is cyclohexyl 4-amino-1-benzyl isonipecotate (8n) whose I.D.50 is about $4 \times 10 \ 10^{-7}m$, which means that 50 m/ of a $4 \times 10^{-7}m$ solution of deamino-ester 8n (i.e., 11 μg of dioxalate) inhibit the growth of 5 g of lentils by a factor of 50%. This compound has a herbicidal activity equal to that of 2-4-D on the growth of lentils, but its action on dicotyledons is more specific than that of 2-4-D.

TABLE 1

Inhibiting activity of alkyl 4-amino-1-benzyl isonipecotates (8) on the growth of lentils and Rye-Grass

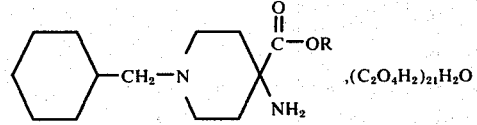

,$(C_2O_4H_2)_{2\frac{1}{2}}H_2O$

| R | Product reference | I.D. 50 Lentils | Rye Grass |
|---|---|---|---|
| H | 7a | $>4 \times 10^{-3}M$ | $>>10^{-3}M$ |
| Me | 8a | $2.55 \times 10^{-3}M$ | $>>10^{-3}M$ |
| Et | 8b | $1.4 \times 10^{-3}M$ | $3.5 \times 10^{-3}M$ |
| n-Pr | 8c | $5.5 \times 10^{-5}M$ | $10^{-3}M<I.D.50<2 \times 10^{-3}M$ |
| iso-Pr | 8d | $3 \times 10^{-5}M$ | — |
| n-Bu | 8e | $6 \times 10^{-6}M$ | $5 \times 10^{-4}M<I.D.50<10^{-3}M$ |
| iso-Bu | 8f | $6 \times 10^{-6}M$ | — |
| 1-Pentyl | 8g | $3 \times 10^{-6}M$ | — |
| 1-Hexyl | 8h | $5 \times 10^{-6}M$ | — |
| 1-Heptyl | 8j | $8 \times 10^{-5}M$ | — |
| 1-Octyl | 8k | $1.75 \times 10^{-4}M$ | $5 \times 10^{-4}M<I.D.50<10^{-3}M$ |
| 1-Decyl | 8l | $2.75 \times 10^{-4}M$ | — |
| 1-Dodecyl | 8m | $1.0 \times 10^{-3}M$ | $10^{-3}M<I.D.50<2 \times 10^{-3}M$ |
| Cyclohexyl | 8n | $4 \times 10^{-7}M$ | $10^{-4}M<I.D.50<10^{-3}M$ |
| 2-Phenethyl | 8p | $3.75 \times 10^{-4}M$ | — |
| 2-4-D | — | $3.5 \times 10^{-7}M$ | $6 \times 10^{-5}M$ |
| Diuron | — | $3 \times 10^{-3}M$ | $>5 \times 10^{-3}M$ |

Post-emergence efficiency of cyclohexyl 4-amino-1-benzyl isonipecotate

The high pre-emergence inhibiting activity of cyclohexyl 4-amino-1-benzyl isonipecotate on the growth of lentils led to post-emergence experimentation.

FIG. 2 gives the post-emergence efficiency of cyclohexyl 4-amino-1-benzyl isonipecotate on the growth of lentils (Lens esculenta) at different concentrations.

When 10 ml of a $1 \times 10^{-3}M$ solution of diamino-ester (8n)(i.e., 5.1 mg) are sprayed on 5 g of growing lentils after these have been exposed to light during two days, the growth of the stemlets is stopped within 5 days, to give a final inhibition of 86% (by weight).

Interruption of the growth of stems with 10 ml of a $2 \times 10^{-5}M$ solution of the same compound (100 μg) occurs more slowly, but is complete seven days after spraying the herbicidal solution.

When the herbicide is sprayed only three days after exposure of the seeds to light, the slowdown of the growth of the stems is less marked.

To conclude, it should be noted that cyclohexyl 4-amino-1-benzyl isonipecotate checks very rapidly the elongation of the growing lentil stems, without affecting either the phototropism or the chlorophyllian function, as efficiently as sodium 2,4-dichlorophenoxyacetate.

Table 2 sets forth the inhibiting activity of other compounds of the formula (I) on the growth of lentils.

TABLE 2

$$Z-N\underset{}{\overset{}{\diagdown}}\underset{}{\overset{COR^1}{\diagup R^2}}$$
(piperidine ring with COR¹, and N(R²)(R³) substituents at position 4)

| R¹ | Z | $\underset{R^3}{\overset{R^2}{N{-}}}$ | Pre-emergence I.D.50 (lentils) |
|---|---|---|---|
| —O CH₂CH₃ | Ph—CH₂— | —NH₂ | $1.4 \times 10^{-3}$ M |
| | | —NHCO—Ph | $1.6 \times 10^{-3}$ M |
| | | —NH—CO—Me | $4.7 \times 10^{-3}$ M |
| | | —NH—CO—NH—Ph | $7.5 \times 10^{-4}$ M |
| | | phthalimido (—N(CO)₂C₆H₄) | $1.4 \times 10^{-3}$ M |
| | | succinimido-type $-N(CO-CH_2)_2$ | $1.5 \times 10^{-3}$ M |
| —OCH₃ | H | —NH₂ | $4 \times 10^{-3}$ M |
| | Ph—CH₂— | —NH₂ | $1.5 \times 10^{-3}$ M |
| | | —NH—CO—Ph | $2.55 \times 10^{-3}$ M |
| N-butoxy | Ph—CH₂— | —NH₂ | $6 \times 10^{-6}$ M |
| | | —NH—CO—Ph | $6 \times 10^{-4}$ M |
| | | —NH—CH₂—Ph | $4 \times 10^{-5}$ M |
| | p-Cl—Ph—CH₂ | —NH₂ | $8 \times 10^{-6}$ M |
| 1-pentyloxy | H | —NH₂ | $1.25 \times 10^{-3}$ M |
| | Ph—CH₂— | —NH₂ | $3 \times 10^{-6}$ M |
| Cyclohexyloxy | H | —NH₂ | $9.5 \times 10^{-4}$ M |
| | Ph—CH₂— | —NH₂ | $4 \times 10^{-7}$ M |
| | | —NH—CO—NH—Ph | $5 \times 10^{-4}$ M |
| | p-Cl—Ph—CH₂ | —NH₂ | $8 \times 10^{-7}$ M |
| —NH₂ | Ph—CH₂— | —NH₂ | $> 2 \times 10^{-3}$ M |
| —NH—NH₂ | Ph—CH₂— | —NH₂ | $5.5 \times 10^{-4}$ M |

It is apparent from these various tests that the compounds of the formula (I) have a most substantial inhibiting activity on the germination and the growth of lentils (dicotyledons), said activity being much lower in the case of Rye-Grass (monocotyledons).

The herbicidal activity of such diamino-esters is closely related to the nature of the alkyl radical which esterifies the carboxyl function; while it is as active as Diuron on the growth of lentils, the methyl ester is 6500 times less herbicidal than the cyclohexyl ester whose efficiency is closely similar to that of 2,4 D.

The usefulness of said compounds is due:

To the specificity of their action: they inhibit the growth of some dicotyledons (lentils) without affecting that of monocotyledons (Rye-Grass).

To their low toxicity: in mice, the "lethal dose 50%" of these diamino-esters is comprised within the range from 100 to 700 mg/kg (on intraperitoneal injection); that of 2,4 D is 375 mg/kg (per os).

To the fact that, at low dosages, their action does not affect the harmonious development of the plants. Indeed, such alkyl 4-amino-1-benzyl isonipecotates do not have any influence on the chlorophyllian function, on phototripism, and do not induce an erratic growth of the treated plants, as in the case of 2,4-D.

On the other hand, these compounds which have both pre- and post-emergence efficiency, do not appear to have any deleterious influence on bacterial growth; therefore, it may be assumed that such diamino-esters are biodegradable and will not accumulate in the soil.

The following non-limiting examples are given to illustrate the preparation of the compounds.

The melting points of the synthetically produced materials are determined over a Kofler block previously calibrated with the reference materials. The Rf values given correspond to chromatographic analyses effected unless otherwise indicated) according to the ascending technique, in the upper phase of a n-butanol-acetic acid-water (4:1:5) mixture, over 0.25 mm thick Silicagel G (Merck) plates.

A. PREPARATION OF STARTING MATERIALS DERIVED FROM PIPERIDYL-SPIROHYDANTOINS

Preparation of 1-benzyl-4-piperidone

N,N-di-(2-carboxymethoxy-ethyl)benzylamine (3a) is prepared, in a yield of 83%, by action of methyl acrylate on benzylamine (3).

| B.p. | = 150–60° C/0.5 mm | Literature: | B.p. | = 139° C/0.2 mm |
|---|---|---|---|---|
| $n_D^{23}$ | = 1.501 | | $n_D^{20}$ | = 1.501 |

The above amine (3a) may undergo a Dieckmann cyclization under the action of sodium, sodium hydride or sodium ethoxide. Tests were conducted with the various methods. The most useful, however, appears to be that using sodium methoxide which provides 1-benzyl-3-carbomethoxy-4-piperidone (4a) in good yields. On subsequent treatment with hydrochloric acid, the latter is decarboxylated to 1-benzyl-4-piperidone (5a) in a yield of 58%.

| B.p. | = 118–25° C/1–2 mm | Literature: | B.p. | = 144–6° C/0.3 mm |
|---|---|---|---|---|
| $n_D^{20}$ | = 1.541 | | $n_D^{23}$ | = 1.5374 |

Preparation of 1-(p-chloro-benzyl)-4-piperidone

When using p.chlorobenzylamine instead of benzylamine, the same techniques gives N,N-di-(2-carboxymethyl-ethyl)-p.chloro-benzyl(36) amine (in a yield of 81%) whose oxalate melts at 153° C (EtOH).

|  | C | H | N | Cl |
|---|---|---|---|---|
| Analysis: for $C_{14}H_{16}ClN_3O_2$: | | | | |
| Calculated %: | 57.24 | 5.49 | 14.31 | 12.07 |
| Found %: | 57.21 | 5.44 | 14.11 | 11.89 |

|  | C | H | N | Cl |
|---|---|---|---|---|
| Analysis, for $C_{15}H_{20}ClNO_4, C_2O_4H_2$ | | | | |
| Calculated %: | 50.53 | 5.49 | 3.47 | 8.78 |
| Found %: | 50.74 | 5.55 | 3.68 | 8.84 |

N,N-di-(2-carboxymethoxy-ethyl)-p.chloro-benzylamine (3b) is treated in the same manner as its non-chlorinated analog (3a) to give 49% of 1-(p.chloro-benzyl)-4-piperidone whose oxalate melts at 192° C (EtOH). Base: B.p. = 150–2° C/1 mm; $n_D^{28}$ = 1.545

|  | C | H | N | Cl |
|---|---|---|---|---|
| Analysis: for $C_{12}H_{14}ClNO, C_2O_4H_2$ | | | | |
| Calculated %: | 53.59 | 5.14 | 4.47 | 11.30 |
| Found %: | 53.39 | 5.15 | 4.57 | 11.65 |

Preparation of 8-benzyl-1,3,8-triazaspiro-(4,5)-decane-2,4-dione (6a)

A mixture of 1-benzyl-4-piperidone (70 g; 0.37 M), sodium cyanide (49 g; 1.0 M) and ammonium carbonate (342 g; 3.0 M) in one liter of 50% aqueous-alcoholic solution is stirred at 60° C during 12 hours. The inorganic salts dissolve gradually in the solution in which white spirohydantoin (6a) crystals are formed. These are then suction filtered through sintered glass, thoroughly washed with water and then recrystallized from 80% ethanol to give, after drying in vacuo, a yield in excess of 90%.

The resulting material melts at 283–5° C, whereas that described by G. Winters melts at 280–2° C.

|  | C | H | N |
|---|---|---|---|
| Analysis: for $C_{14}H_{17}N_3O_2$ | | | |
| Calculated %: | 64.84 | 6.61 | 16.21 |
| Found %: | 64.92 | 6.62 | 15.97 |

Preparation of 8-(p-chloro-benzyl)-1,3,8-triazaspiro-(4,5)decane-2,4-dione (6b)

1-(p-Chloro-benzyl)-4-piperidone 5b reacts in the same manner with sodium cyanide and ammonium carbonate to give 92% 8-(p-chlorobenzyl)-1,3,8-triazaspiro-(4,5)-decane-2,4-dione (6b).

B. PREPARATION OF 4-amino-1-benzyl isonipecotic acids

A suspension of 8-benzyl-1,3,8-triazaspiro-(4,5)decane-2,4-dione (6a) (26.0 g; 0.10 M) and barita hydrate (126 g; 0.40 M) in water (300 ml) is heated at 160° C, during 3 hours, under a saturating vapour pressure. After cooling, the barium carbonate formed in the course of the hydrolysis is filtered off and the filtrate is adjusted at pH 3–4 by slowly adding a 5N sulfuric acid solution. The resulting baryum sulfate is filtered off and the aqueous filtrate is evaporated to dryness, by heating over the water-bath, under reduced pressure. After recrystallization from a 50% aqueous-alcoholic solution, the solid white residue gives 29.5 g (Yield = 89%) of 4-amino-1-benzyl isonipecotic acid sulfate M.p. = 289–91° C (dec.); Rf = 0.14.

Using the same technique, 8-(p.chloro)benzyl-1,3,8-triazaspiro(4,5)decane-2,4-dione (6b) may be hydrolyzed to 4-amino-1-(p.chloro) benzyl isonipecotic acid sulfate, in a yield of 78%. M.p. = 290° C (dec.) ; Rf = 0.13.

EXAMPLE 1

Ethyl 4-amino-1-benzyl isonipecotate (8b)

The solution obtained from the mixture of 10.8 g (0.050 M) 4-amino-1-benzyl isonipecotic acid sulfate and 400 ml anhydrous ethanol, saturated with gaseous hydrogen chloride, is refluxed during 15 hours. Excess ethanol is then evaporated in vacuo and the solid white residue is dissolved in 50 ml water prior to being adjusted to pH 7–8 by addition of sodium bicarbonate. Ester (8b) is then extracted with ether; the ether extracts are combined to give a solution which is dried overnight over anhydrous sodium sulfate and is then filtered and concentrated in vacuo, to leave 12.9 g (Yield = 83%) of a slightly yellow oil. The latter may then be converted to the hydrogen dioxalate monohydrate by addition of oxalic acid in acetone solution. M.p. = 156–8° C (MeOH); Rf = 0.21.

EXAMPLE 2

Methyl 4-amino-1-benzyl isonipecotate (8a)

4-Amino-1-benzyl isonipecotic acid sulfate (18.2 g; 0.055 M) is refluxed during 15 hours in anhydrous methanol (200 ml) saturated with gaseous hydrogen chloride, to give a clear solution which is then concentrated in vacuo, leaving a solid white residue. The latter is treated according to the aforedescribed technique, to give 10.5 g (Yield = 77%) of methyl 4-amino-1-benzyl isonipecotate. Oxalate: M.p. = 151–2° C (MeOH); Rf = 0.20.

EXAMPLE 3 n-Propyl 4-amino-1-benzyl isonipecotate (8c)

This ester is obtained in a yield of 65% after refluxing acid (7a) during fifteen hours in absolute propanol saturated with gaseous hydrogen chloride.
Oxalate: M.p. = 200° C (MeOH); Rf = 0.31.

EXAMPLE 4 iso-Propyl 4-amino-1-benzyl isonipecotate (8d)

4-Amino-1-benzyl isonipecotic acid sulfate (5.0 g; 0.015 M) is refluxed during 7 hours in absolute isopropanol (100 ml) saturated with gaseous hydrogen chloride, to give 4.3 g (Yield = 60%) isopropyl 4-amino-1-benzyl isonipecotate hydrogen dioxalate monohydrate. M.p. = 204° C (MeOH); Rf = 0.25.

EXAMPLE 5 n-Butyl 4-amino-1-benzyl isonipecotate (8e)

This ester is obtained, as described in the previous examples, by refluxing acid 7a during 15 hours in absolute n-butanol saturated with gaseous hydrogen chloride. Yield = 62%. Oxalate: M.p. = 210–1° C (MeOH); Rf = 0.47.

EXAMPLE 6 iso-Butyl 4-amino-1-benzyl isonipecotate (8f)

This ester is obtained in a yield of 56% after refluxing acid 7a) during 15 hours in isobutanol.
Oxalate: M.p. = 211° C(MeOH).

EXAMPLE 7

1-Pentyl 4-amino-1-benzyl isonipecotate (8g)

Acid (7a) is esterified with pentyl alcohol. After refluxing (138° C) during seven hours, ester (8g) is obtained in a yield of 50%. Oxalate: M.p. = 211° C (EtOH); Rf = 0.60.

EXAMPLE 8

1-Hexyl 4-amino-1-benzyl isonipecotate (8h)

4-Amino-1-benzyl isonipecotic acid (7a) is refluxed during seveeen hours in 1-hexanol (100 ml) saturated with gaseous hydrogen chloride; to give 1-hexyl 4-amino-1-benzyl isonipecotate (8h) in a yield of 20%.
Oxalate: M.p. = 193° C (EtOH).

EXAMPLE 9

1-Heptyl 4-amino-1-benzyl isonipecotate (8j)

Refluxing during 6 hours (175° C) in 1-heptyl alcohol is sufficient to esterify acid (7a) to 1-heptyl 4-amino-1-benzyl isonipecotate in a yield of 28%.
Oxalate: M.p. = 158° C (EtOH); Rf = 0.55.

EXAMPLE 10

1-Octyl 4-amino-1-benzyl isonipecotate (8k)

Acid (7a) is refluxed (194–5° C) during three hours in 1-octanol (100 ml) saturated with gaseous hydrogen chloride, to give ester (8k) in a yield of 25% (after two recrystallizations from methanol).
Esterification of 4-amino-1benzyl isonipecotic acid (7a) M.p. = 114–5° C (MeOH); Rf = 0.64.

EXAMPLE 11

1-Decyl 4-amino-1-benzyl isonipecotate (8l) with 1-decyl alcohol requires heating during eight hours over an oil bath at 125° C. Ester (8l) is obtained in a yield of about 40%.

Oxalate: M.p. = 121–2° C (EtOH); Rf = 0.65.

EXAMPLE 12

1-Dodecyl 4-amino-1-benzyl isonipecotate (8m)

A mixture of 4-amino-1-benzyl isonipecotic acid sulfate (3.3 g; 0.010 M) and 22.4 g (0.12 m) 1-dodecanol saturated with gaseous hydrogen chloride is heated at 125° C during eight hours.

The resulting ester is highly soluble in ether (even in acidic medium). After evaporation of the ether and the excess dodecanol, the residual yellow oil is converted to the oxalate which is recrystallized three times from methanol and is obtained in a yield of 48%.

Oxalate: M.p. = 120–1° C (MeOH); Rf = 0.57.

EXAMPLE 13

Cyclohexyl 4-amino-1-benzyl isonipecotate (8n)

Amino-acid (7a) 13.2 g; 0.040 M) is refluxed during 12 hours in cyclohexanol (150 ml) saturated with gaseous hydrogen chloride, to give 8.1 g (Yield = 65%) cyclohexyl 4-amino-1-benzyl isonipecotate.

Oxalate: M.p. = 221–2° C (MeOH); Rf = 0.39.

EXAMPLE 14

2-Phenylethyl 4-amino-1-benzyl isonipecotate (8p)

This ester, obtained in a yield of 20%, is prepared by refluxing acid (7a) during 3 hours in an excess of 2-phenylethyl alcohol in hydrochloric solution.

After evaporating off the excess alcohol, ester (8p) is extracted with ether at pH 7–8. Oxalate: M.p. = 160° C (MeOH); Yield = 20%; Rf = 0.61.

EXAMPLE 15 n-Butyl 4-amino-1-(p.chlorobenzyl)-isonipecotate (8q)

This ester is prepared from 4-amino-1-(p.chlorobenzyl)-isonipecotic acid (7b) by refluxing during fifteen hours in an excess of n-butanol saturated with gaseous hydrogen chloride. The yield of this esterification is 40%.

Oxalate: M.p. = 209° C (MeOH); Rf = 0.43

EXAMPLE 16

Cyclohexyl 4-amino-1-(p.chloro-benzyl)isonipecotate (8r)

This compound is obtained synthetically, according to the aforedescribed technique, by esterification of 4-amino-1-(p.chlorobenzyl)isonipecotic acid (7b) with cyclohexyl alcohol. The reaction is complete after refluxing during ten hours and gives ester (8r) in a yield of 47%.

Oxalate: M.p. = 203° C (MeOH); Rf = 0.52

EXAMPLE 17

Ethyl 4-(N-benzoylamino)-1-benzyl isonipecotate (11b)

The dropwise addition of benzoyl chloride (4.7 ml; 0.040 M) to a solution of ethyl 4-amino-1-benzyl isonipecotate (8b)(10.5 g; 0.040 M) and triethylamine (4.0 g; 0.040 M) in anhydrous toluene (250 ml) produces an abundant white triethylamine hydrochloride precipitate (M.p. = 253–4° C. and a sudden heating of the solution. The reaction mixture is heated to refluxing temperature during ½ hour and is then cooled and filtered: the white triethylamine hydrochloride precipitate is washed twice with anhydrous toluene, after which the filtrate is concentrated by heating under reduced pressure.

The solid white residue (14.2 g; Yield = 97%) is recrystallized from anhydrous acetone-petroleum ether, to give 12.5 g (Yield = 85%) ethyl-4-(N-benzoylamino)-1-benzyl isonipecotate (11b).

| Base: | M.p. =127° C (Me₂CO/petroleum ether) | Rf =0.61 |
|---|---|---|
| Oxalate: | M.p. =217° C (MeOH) | Rf =0.66 |

EXAMPLE 18

Methyl 4-(N-benzoylamino)-1-benzyl isonipecotate (11a)

Benzoylation of methyl 4-amino-1-benzyl isonipecotate (8a) according to the technique described in Example 17 gives compound (11a) in a yield of 83%.

Oxalate: M.p. = 173–5° C (MeOH); Rf = 0.61.

EXAMPLE 19 n-Butyl 4-(N-benzoylamino)-1-benzyl isonipecotate (11c)

On treatment with equimolar amounts of benzyl chloride and triethylamine, n-butyl 4-amino-1-benzyl isonipecotate (8e) is converted to n-butyl 4-(N-benzoylamino)-1-benzyl isonipecotate (11c) in a yield of 50%.

Oxalate: M.p. = 212° C (MeOH); Rf = 0.76.

EXAMPLE 20

Ethyl 4-(N-acetamido)-1-benzyl isonipecotate (10a)

Ethyl 4-amino-1-benzyl isonipecotate (8b) (7.2 g; 0.027 M) and sodium acetate (7.2 g; 0.088 M) molten in acetic anhydride (100 ml) are heated during one hour over a boiling water-bath, to give an orange solution. Evaporation of the excess acetic anhydride leaves a solid orange residue which is dissolved in water (100 ml). This aqueous solution is washed repeatedly with ether and is then adjusted to pH 10–11 by addition of sodium hydroxide and extracted with chloroform. The organic extracts are combined to give a solution which is dried overnight over sodium sulfate and is then filtered and concentrated in vacuo. The solid orange residue (7.0 g; Yield = 84%) is recrystallized from anhydrous acetone, to give 5.1 g (Yield = 61%) ethyl 4-(N-acetamido)-1-benzyl isonipecotate (10a).

| Base: | M.p. =143° C (Me₂CO) | Rf =0.65 |
|---|---|---|
| Oxalate: | M.p. =185° C (MeOH) | |

EXAMPLE 21 n-Butyl 4-(N-acetamido)-1-benzyl isonipecotate (10b)

Treatment of n-butyl 4-amino-1-benzyl isonipecotate (8e) with excess acetic anhydride in the presence of sodium acetate, according to the technique described in the preceding example, gives n-butyl 4-(N-acetamido)-1-benzyl isonipecotate (10b) in a yield of 53%.

Oxalate: M.p. = 197° C (MeOH); Rf = 0.57.

| | C | H | N |
|---|---|---|---|
| Analysis: for $C_{19}H_{28}N_2O_3,C_2O_4H_2$ | | | |
| Calculated %: | 59.70 | 7.16 | 6.63 |
| Found %: | 59.60 | 7.12 | 6.65 |

EXAMPLE 22

Ethyl 1-benzyl-4-(N-phthaloylamino)-isonipecotate (13)

A solution of ethyl 4-amino-1-benzyl isonipecotate (8b) (12.2 g; 0.046 M), phthalic anhydride (7.0 g;

0.047 M) and triethylamine (0.5 ml) in anhydrous toluene (300 ml) is refluxed during 16 hours, a water separator being provided between the flask and the cooling device.

Evaporation of the toluene leaves a yellow oily residue which is converted to the oxalate, by addition of 10 ml of acetone solution saturated with oxalic acid. The pasty residue obtained after evaporation of the acetone is triturated with anhydrous ether, to give an abundant white precipitate which, on recrystallization from methanol, gives 20.7 g (Yield = 92%) ethyl 1-benzyl-4-(N-phthaloylamino)-isonipecotate hydrogen oxalate M.p. = 199°–200° C (MeOH); Rf = 0.70.

EXAMPLE 23

Ethyl 1-benzyl-4-(N-succinimido)-isonipecotate (14)

Ethyl 1-benzyl-4-(N-succinimido)isonipecotate (14) may be obtained in a yield of 55%, using the technique just described for the synthesis of the N-phthaloyl compound, by refluxing during 15 hours equimilar amounts of ethyl 4-amino-1-benzyl isonipecotate (8b) and succinic anhydride in the presence of a few drops of triethylamine.

Oxalate: M.p. = 130–1° C (MeOH); Rf = 0.41.

EXAMPLE 24

Ethyl 1-benzyl-4-(3'-phenyl-1'-ureido)-isonipecotate (12a)

A solution of ethyl 4-amino-1-benzyl isonipecotate (8b) (5.2 g; 0.020 M), phenyl isocaynate(2.4 g; 0.020 M) and triethylamine (0.10 ml) in anhydrous ether (150 ml) is stirred overnight at room temperature. The white precipitate formed during the reaction is then suction filtered through sintered glass, washed twice with ether and recrystallized from anhydrous acetone (100 ml), to give 6.4 g (Yield = 84%) ethyl 1-benzyl-4-(3'-phenyl-1'-ureido)isonipecotate (12a).

M.p. = 178–9° C (Me$_2$CO); Rf = 0.66.

EXAMPLE 25 n-Butyl 1-benzyl-4-(3'-phenyl-1'-ureido)-isonipecotate (12b)

The synthesis of compound (12b) may be effected in a yield of 49% according to the technique described in Example 24, by action of phenyl isocyanate on n-butyl 4-amino-1-benzyl isonipecotate (8e) dissolved in anhydrous ether.

M.p. = 147° C (Me$_2$CO); Rf = 0.82.

| | C | H | N |
|---|---|---|---|
| Analysis: for C$_{24}$H$_{31}$N$_3$O$_3$: | | | |
| Calculated %: | 70.38 | 7.63 | 10.26 |
| Found %: | 70.30 | 7.68 | 10.32 |

EXAMPLE 26

Cyclohexyl 1-benzyl-4-(3'-phenyl-1'-ureido)isonipecotate (12c)

Cyclohexyl 4-amino-1-benzyl isonipecotate (8n), when treated in the same manner with phenyl isocyanate, is converted to cyclohexyl 1-benzyl-4-(3'-phenyl-1'-ureido)-isonipecotate (12c) in a yield of 55%.

M.p. = 185° C (Me$_2$CO).

EXAMPLE 27

Ethyl 4-amino-isonipecotate (9a)

A solution of 7.5 g (0.016 M) ethyl 4-amino-1-benzyl isonipecotate (8b) hydrogen oxalate in 300 ml ethanol is hydrogenated at 55° C and at atmospheric pressure in the presence of 0.8 g of 5% Pd/C.

After stirring 48 hours with a magnetic stirrer, hydrogen absorption has completely ceased: the solution is filtered hot and is then evaporated to dryness, by heating under reduced pressure. The solid white residue gives 3.5 g (Yield = 58%) ethyl 4-aminoisonipecotate (9a) on recrystallization from 50% ethanol.

Oxalate: M.p. = 118–20° C (EtOH).

EXAMPLE 28 n-Butyl 4-amino-isonipecotate (9b) is obtained synthetically in a yield of 62%, using the procedure of Example 27, by catalytic debenzylation of n-butyl 4-amino-1-benzyl isonipecotate (8e).

Oxalate: M.p. 32 188° C (EtOH); Rf = 0.12.

EXAMPLE 29

1-Pentyl 4-amino-isonipecotate (9c)

Catalytic hydrogenation of 1-pentyl 4-amino -1-benzyl isonipecotate (8g) in alcohol solution, under the usual conditions, provides the corresponding N-debenzylated amino-ester (9c) in a yield of 61%.

Oxalate: M.p. = 180–1° C. (EtOH/ $_2$O); Rf = 0.25.

EXAMPLE 30 n-Butyl 1-benzyl-4-(N-benzyl)amino-isonipecotate (15)

A solution of n-butyl 4-amino-1-benzyl isonipecotate (8e)(1.45 g; 5.0 mM), benzyl chloride (0.7 g; 5.5 mM) and triethylamine; (1 g; 10 mM) is refluxed in anhydrous toluene (80 ml) during 20 hours. The mixture is then filtered, concentrated in vacuo, made alkaline and repeatedly extracted with ether. Evaporation of the ether leaves 1.9 g of a brown oil which is converted to the oxalate by addition of oxalic acid in acetone solution. The oxalate is triturated with anhydrous ether (50 ml), after which it is filtered and then recrystallized from anhydrous methanol (30 ml), to give 1.3 g (Yield = 47%) of compound (15).

M.p. = 187° C (MeOH); Rf = 0.62.

| | C | H | N |
|---|---|---|---|
| Analysis: C$_{24}$H$_{32}$N$_2$O$_2$,(C$_2$O$_4$H$_2$)$_2$ | | | |
| Calculated %: | 59.99 | 6.47 | 5.00 |
| Found %: | 59.81 | 6.56 | 4.91 |

EXAMPLE 31

4-Amino-1-benzyl-4-carbazoyl piperidine (17)

A solution of ethyl 4-amino-1-benzyl isonoipecotate (8b) (1.3 g; 5 mM) and hydrazine (5.0 g; 0.10 M) in absolute ethanol (50 ml) is refluxed during 27 hours. The solution is then cooled and evaporated to dryness: the white solid residue is converted to the oxalate which is washed with ether and then recrystallized from anhydrous methanol, to give 0.9 g (Yield = 41%) 4-amino-1-benzyl-4-carbazoyl piperidine (17) oxalate.

M.p. = 231° C (MeOH); Rf = 0.13.

| | C | H | N |
|---|---|---|---|
| Analysis: for C₁₇H₂₀N₄O,(C₂O₄H₂)₂,H₂O | | | |
| Calculated %: | 45.73 | 5.87 | 12.55 |
| Found %: | 45.95 | 5.93 | 11.80 |

Having now described our invention what we claim as new and desire to secure by Letters Patent is:

1. A process for controlling the growth of dicotyledons, which comprises applying to the seeds prior to or after their germination a herbicidally effective amount of a compound of the formula:

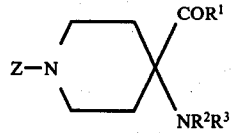

wherein Z is selected from the group consisting of hydrogen, benzyl, or parachlorobenzyl, R' is a group OR in which R is selected from the group consisting of alkyl groups having a from 1 to 12 carbon atoms, cyclohexyl, and lower phenylalkyl; and $R^2$ and $R^3$ are selected from the group consisting of hydrogen, benzyl, and their acid addition salts of non-phytotoxic acids acceptable in agriculture.

2. A process according to claim 1, in which said compound is cyclohexyl 4-amino-1-benzyl isonipecotate.

3. A process according to claim 1, in which the acid addition salts acceptable in agriculture are selected from the group consisting of sulfate and oxalate.

* * * * *